US011972570B2

(12) United States Patent
Hasegawa

(10) Patent No.: US 11,972,570 B2
(45) Date of Patent: Apr. 30, 2024

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Yu Hasegawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 413 days.

(21) Appl. No.: 17/349,930

(22) Filed: Jun. 17, 2021

(65) Prior Publication Data

US 2021/0312631 A1 Oct. 7, 2021

Related U.S. Application Data

(63) Continuation of application No. PCT/JP2019/049421, filed on Dec. 17, 2019.

(30) Foreign Application Priority Data

Dec. 18, 2018 (JP) ................................ 2018-236662

(51) Int. Cl.
*G06T 7/11* (2017.01)
(52) U.S. Cl.
CPC ...... *G06T 7/11* (2017.01); *G06T 2207/20104* (2013.01)
(58) Field of Classification Search
CPC . G06T 2207/10072; G06T 2207/20104; G06T 2207/30004; G06T 7/11; A61B 5/055; A61B 6/03
See application file for complete search history.

(56) References Cited

U.S. PATENT DOCUMENTS 5,431,161 A * 7/1995 Ryals ..................... G16H 40/63
600/428
6,993,174 B2 1/2006 Fan et al.
(Continued)

FOREIGN PATENT DOCUMENTS

JP 2003180678 7/2003
JP 2005073817 3/2005
(Continued)

OTHER PUBLICATIONS

Oscar Jimenez-del-Toro, "Cloud-Based Evaluation of Anatomical Structure Segmentation and Landmark Detection Algorithms: VISCERAL Anatomy Benchmarks," Jun. 9, 2016 , IEEE Transactions On Medical Imaging, vol. 35, No. 11, Nov. 2016, pp. 2462-2471.*
(Continued)

*Primary Examiner* — Omar S Ismail
(74) *Attorney, Agent, or Firm* — JCIPRNET

(57) ABSTRACT

There is provided an image processing apparatus comprising: a processor that is configured to: acquire a segmentation image obtained by segmenting a target image into a plurality of regions; accept position information indicating a position specified by a user on the segmentation image; acquire on the basis of image information, preference levels of the plurality of regions from which a region to be assigned to the position on the segmentation image indicated by the position information is selected; and perform control to display on a display, candidates for the region to be assigned so as to allow selection of the region to be assigned, on the basis of the acquired preference levels.

16 Claims, 7 Drawing Sheets

(56) References Cited

U.S. PATENT DOCUMENTS

| | | | | |
|---|---|---|---|---|
| 7,987,111 | B1* | 7/2011 | Sharma | G06Q 30/02 |
| | | | | 705/7.29 |
| 8,577,115 | B2 | 11/2013 | Gering et al. | |
| 8,774,483 | B2 | 7/2014 | Yoshida et al. | |
| 11,276,175 | B2* | 3/2022 | Witte | G06T 7/0012 |
| 11,547,499 | B2* | 1/2023 | Geri | A61B 34/20 |
| 2002/0081603 | A1* | 6/2002 | Wolffe | C12N 15/66 |
| | | | | 435/6.12 |
| 2002/0126884 | A1* | 9/2002 | Gerritsen | G06T 17/00 |
| | | | | 382/131 |
| 2003/0129603 | A1* | 7/2003 | Wolffe | C12N 15/66 |
| | | | | 536/25.4 |
| 2008/0317314 | A1* | 12/2008 | Schwartz | G06T 7/0012 |
| | | | | 382/131 |
| 2011/0194742 | A1* | 8/2011 | Buelow | G06T 7/11 |
| | | | | 382/128 |
| 2014/0140593 | A1* | 5/2014 | Park | G16Z 99/00 |
| | | | | 382/128 |
| 2015/0146947 | A1* | 5/2015 | Matsumoto | G06F 18/24 |
| | | | | 382/128 |
| 2016/0275674 | A1* | 9/2016 | Rivet-Sabourin | G06T 7/174 |
| 2017/0024397 | A1* | 1/2017 | Laptev | G06F 16/29 |
| 2017/0109915 | A1* | 4/2017 | Kreeger | G06T 7/11 |
| 2018/0315188 | A1* | 11/2018 | Tegzes | G06T 7/11 |
| 2020/0036889 | A1* | 1/2020 | Udayakumar | H04N 23/635 |
| 2021/0147922 | A1* | 5/2021 | Urnov | C12N 9/22 |

FOREIGN PATENT DOCUMENTS

| | | |
|---|---|---|
| JP | 2011512999 | 4/2011 |
| JP | 2011110357 | 6/2011 |
| JP | 2012505008 | 3/2012 |
| JP | 2014100569 | 6/2014 |
| JP | 2015102944 | 6/2015 |

OTHER PUBLICATIONS

Tobias Heimann, "Comparison and Evaluation of Methods for Liver Segmentation From CT Datasets,"Jul. 29, 2009, IEEE Transactions On Medical Imaging, vol. 28, No. 8, Aug. 2009, pp. 1252-1262.*

Karla L Miller, "Multimodal population brain imaging in the UK Biobank prospective epidemiological study,"Sep. 19, 2016, nature NeurneurOScience vol. 19 | No. 11 | Nov. 2016, pp. 1523-1532.*

D. J. McKeefry, "The position and topography of the human colour centre as revealed by functional magnetic resonance imaging," Dec. 1, 1997, Brain (1997), 120, pp. 2230-2240.*

Jimit Doshi, "MUSE: MUlti-atlas region Segmentation utilizing Ensembles of registration algorithms and parameters, and locally optimal atlas selection," Dec. 8, 2015, NeuroImage 127 (2016), pp. 186-193.*

"International Search Report (Form PCT/ISA/210) of PCT/JP2019/049421," dated Mar. 17, 2020, with English translation thereof, pp. 1-5.

"Written Opinion of the International Searching Authority (Form PCT/ISA/237)" of PCT/JP2019/049421, dated Mar. 17, 2020, with English translation thereof, pp. 1-8.

Office Action of Japan Counterpart Application, with English translation thereof, dated Jun. 28, 2022, pp. 1-5.

* cited by examiner

| | DISPLAY PATTERN OF REGION | NAME OF PART | EXISTENCE PROBABILITY |
|---|---|---|---|
| 31 | | PART a | 45% |
| 32 | | PART b | 40% |
| 34 | | PART c | 10% |
| 35 | | BACKGROUND | 4% |
| 33 | | PART d | 1% |

IMAGE PROCESSING APPARATUS, IMAGE PROCESSING METHOD, AND IMAGE PROCESSING PROGRAM

CROSS-REFERENCE TO RELATED APPLICATIONS

This application is a continuation application of International Application No. PCT/JP2019/049421 filed Dec. 17, 2019 the disclosure of which is incorporated herein by reference in its entirety. Further, this application claims priority from Japanese Patent Application No. 2018-236662, filed Dec. 18, 2018, the disclosure of which is incorporated herein by reference in its entirety.

TECHNICAL FIELD

The present disclosure relates to an image processing apparatus, an image processing method, and an image processing program for correcting an assigned region of interest on a segmentation image.

RELATED ART

Recent advancements in medical apparatuses, such as CT (computed tomography) apparatuses and MRI (magnetic resonance imaging) apparatuses, enable diagnosis using high-quality and high-resolution three-dimensional images. For a medical image, such as a CT image acquired by a CT apparatus or an MR image acquired by an MRI apparatus, segmentation for regions of interest, such as organs and lesions, is automatically performed, and the segmented medical image is visualized to help to support diagnosis, treatment, and the like.

Such segmentation is performed by, for example, using an organ auto-segmentation engine using an image processing technology. In such a case where regions of interest are automatically extracted, an over-extracted region or an under-extracted region may appear, and segmentation is not always performed appropriately. In a case where segmentation using an organ auto-segmentation engine fails, an automatically assigned region of interest needs to be corrected manually. However, in a case of making a manual correction, it is necessary to select a region of interest to be assigned to a region that is specified as a region to be corrected. Therefore, as the number of regions of interest assigned as a result of segmentation increases, selection by the user becomes more troublesome.

JP2005-73817A, JP2012-505008A, and JP2003-180678A disclose techniques in which a parameter for adjusting a region of interest obtained as a result of segmentation is adjusted to thereby correct the region of interest.

However, in the techniques described in JP2005-73817A, JP2012-505008A, and JP2003-180678A, a parameter that is a segmentation processing condition is adjusted, and therefore, it is difficult to handle a case where, for example, a user wants to correct a region to which only one region of interest is assigned.

SUMMARY

The present disclosure has been made to enable correction of region assignment as desired by a user while making the user's operation less troublesome.

An image processing apparatus according to the present disclosure includes a processor that is configured to: acquire a segmentation image obtained by segmenting a target image into a plurality of regions; accept position information indicating a position specified by a user on the segmentation image acquire on the basis of image information, preference levels of the plurality of regions from which a region to be assigned to the position on the segmentation image indicated by the position information is selected; and performs control to display on a display, candidates for the region to be assigned so as to allow selection of the region to be assigned, on the basis of the acquired preference levels.

An image processing method according to the present disclosure includes: by a processor, acquiring a segmentation image obtained by segmenting a target image into a plurality of regions;

accepting position information indicating a position specified by a user on the segmentation image;

acquiring on the basis of image information, preference levels of the plurality of regions from which a region to be assigned to the position on the segmentation image indicated by the accepted position information is selected; and performing control to display on a display, candidates for the region to be assigned so as to allow selection of the region to be assigned, on the basis of the acquired preference levels.

Note that non-transitory computer-readable storage medium storing a program for causing a computer to perform the image processing method according to the present disclosure may be provided. Specifically, an image processing program according to the present disclosure causes a computer to:

acquire a segmentation image obtained by segmenting a target image into a plurality of regions;

accept position information indicating a position specified by a user on the segmentation image;

acquire on the basis of image information, preference levels of the plurality of regions from which a region to be assigned to the position on the segmentation image indicated by the accepted position information is selected; and perform control to display on a display, candidates for the region to be assigned so as to allow selection of the region to be assigned, on the basis of the acquired preference levels.

DETAILED DESCRIPTION

Figure 1:
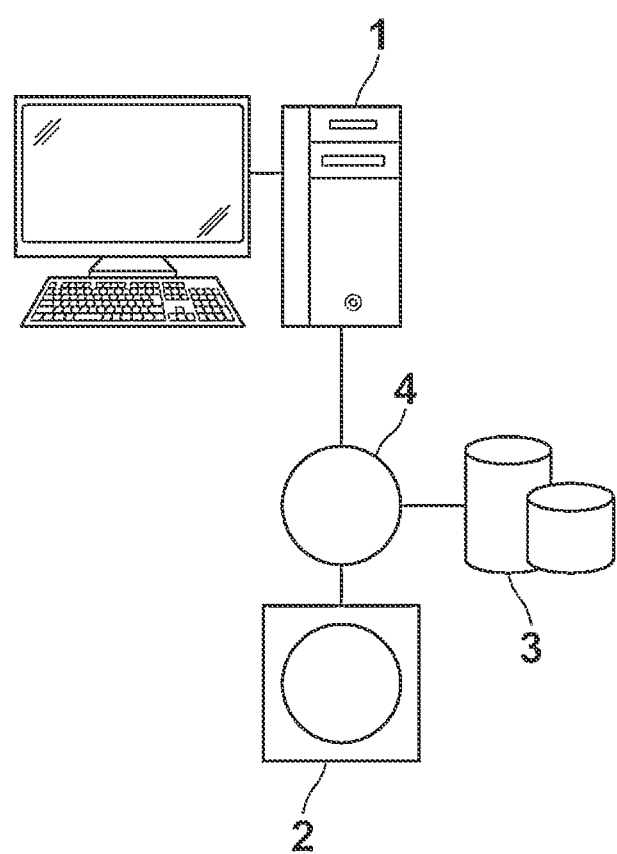
FIG. 1 is a hardware configuration diagram schematically illustrating a diagnosis support system to which an image processing apparatus according to an embodiment of the present disclosure is applied.

Hereinafter, an embodiment of the present disclosure will be described with reference to the drawings. FIG. 1 is a hardware configuration diagram schematically illustrating a diagnosis support system to which an image processing apparatus according to the embodiment of the present disclosure is applied. As illustrated in FIG. 1, in the diagnosis support system, an image processing apparatus 1 according to the present embodiment, a three-dimensional imaging apparatus 2, and an image storage server 3 are connected to each other via a network 4 so as to enable communication.

The three-dimensional imaging apparatus 2 is an apparatus that images a diagnosis target part of a subject to generate a three-dimensional image representing the part, and specifically is a CT apparatus, an MRI apparatus, a PET (positron emission tomography) apparatus, or the like. The three-dimensional image generated by the three-dimensional imaging apparatus 2 is transmitted to the image storage server 3 and saved in the image storage server 3. Note that in the present embodiment, the three-dimensional imaging apparatus 2 is a CT apparatus and generates a CT image including a diagnosis target part of a subject as a three-dimensional image. The three-dimensional image is formed of a plurality of tomographic images. The three-dimensional image corresponds to a target image of the present disclosure.

The image storage server 3 is a computer that saves and manages various types of data and includes an external mass storage device and database management software. The image storage server 3 communicates with other apparatuses via the network 4, which is a wired or wireless network, and transmits and receives image data and the like. Specifically, the image storage server 3 receives various types of data including image data of a three-dimensional image generated by the three-dimensional imaging apparatus 2, and saves the various types of data in a recording medium, such as the external mass storage device, to manage the various types of data. Note that the form of storage of image data and communication between apparatuses via the network 4 conform to a protocol, such as DICOM (Digital Imaging and Communication in Medicine).

The image processing apparatus 1 is configured by installing an image processing program of the present embodiment in one computer. The computer may be a workstation or a personal computer that is directly operated by a doctor who makes a diagnosis or may be a server computer that is connected to the workstation or the personal computer via a network. The image processing program is recorded to a recording medium, such as a DVD (digital versatile disc) or a CD-ROM (compact disc read-only memory) and distributed, and installed in the computer from the recording medium. Alternatively, the image processing program is stored in a storage device of the server computer connected to the network or in a network storage device so as to be externally accessible, downloaded to the computer used by the doctor on request, and installed in the computer.

Figure 2:
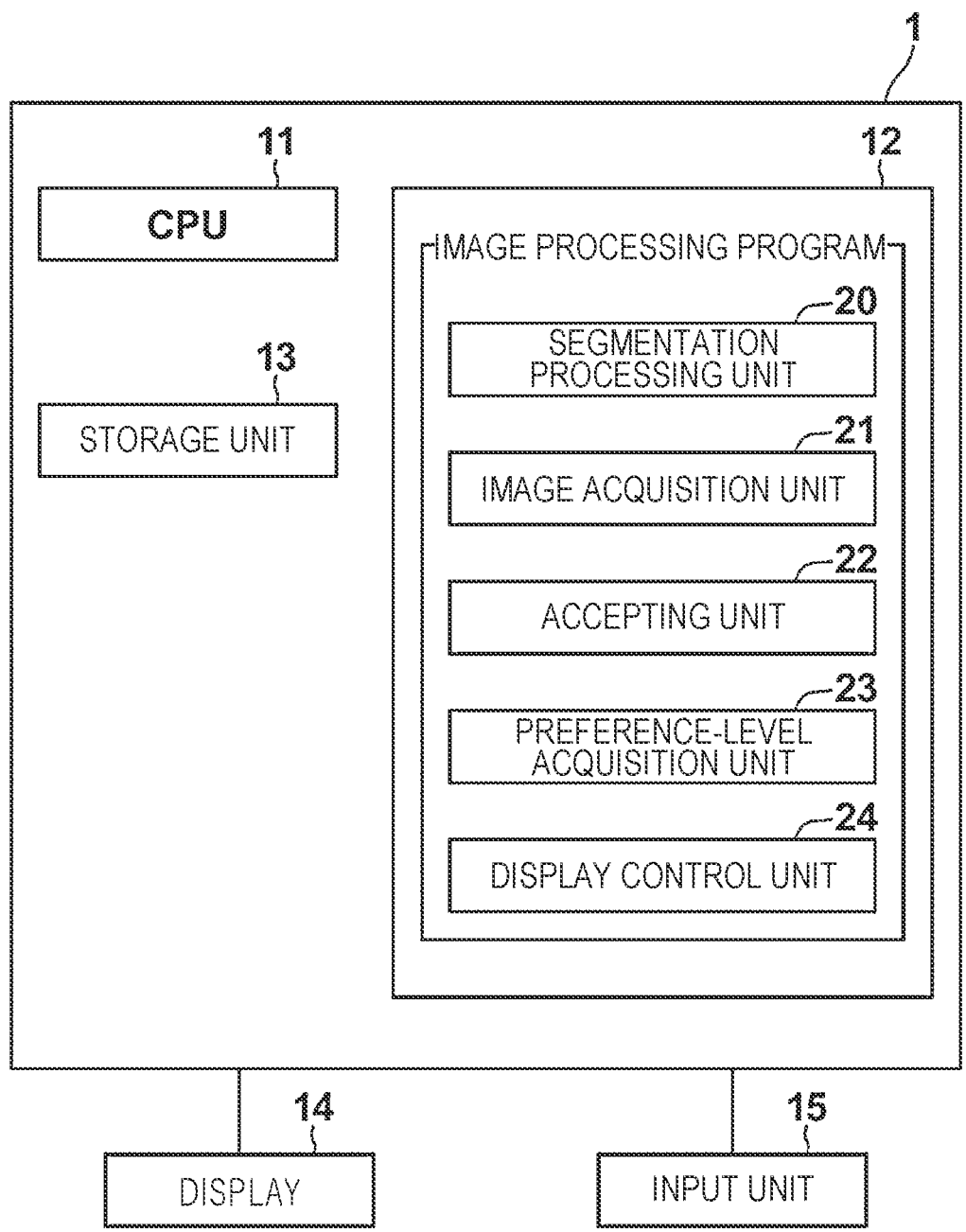
FIG. 2 is a diagram schematically illustrating a configuration of the image processing apparatus according to the embodiment of the present disclosure.

FIG. 2 is a diagram schematically illustrating a configuration of the image processing apparatus implemented by installing the image processing program in the computer. As illustrated in FIG. 2, the image processing apparatus 1 includes a CPU (central processing unit) 11, a memory 12, and a storage unit 13, as in a typical configuration of workstations. To the image processing apparatus 1, a display 14, which is, for example, a liquid crystal display, and an input unit 15, which includes, for example, a keyboard and a mouse, are connected. Note that in the present embodiment, the input unit 15 includes a wheel mouse.

The storage unit 13 is formed of a hard disk drive and the like, in which three-dimensional images acquired from the image storage server 3 via the network 4 and various types of information including information necessary for processing are stored.

In the memory 12, the image processing program is stored. As processes to be performed by the CPU 11, the image processing program defines: a segmentation process for extracting a plurality of regions of interest from a target image and generating a segmentation image obtained by segmenting the target image into a plurality of regions; an image acquisition process for acquiring the segmentation image obtained by segmenting the target image into the plurality of regions; an accepting process for accepting position information indicating a position specified by a user on the segmentation image; a preference-level acquisition process for acquiring on the basis of image information, preference levels of the plurality of regions from which a region to be assigned to the position on the segmentation image indicated by the accepted position information is selected; and a display control process for performing control to display on a display, candidates for the region to be assigned so as to allow selection of the region to be assigned, on the basis of the acquired preference levels.

When the CPU 11 performs these processes in accordance with the program, the computer functions as a segmentation processing unit 20, an image acquisition unit 21, an accepting unit 22, a preference-level acquisition unit 23, and a display control unit 24.

The segmentation processing unit 20 extracts a plurality of regions of interest from a three-dimensional image acquired by the image acquisition unit 21 described below and generates a segmentation image obtained by segmenting the three-dimensional image into a plurality of regions. For this, the segmentation processing unit 20 includes a trained model subjected to machine learning so as to extract regions of interest from a three-dimensional image. The trained model is formed of a neural network, such as a convolutional neural network (CNN) or a recurrent neural network (RNN), subjected to deep learning so as to extract diagnosis target structures, such as organs, bones, and cartilages, as regions of interest. In the present embodiment, the trained model corresponds to a segmentation algorithm of the present disclosure. Examples of diagnosis target organs include the heart, the liver, the lungs, the kidneys, and the brain. In response to input of a three-dimensional image, the trained model outputs the result of determination indicating whether each of the pixels of the three-dimensional image corresponds to a region of interest. The result of determination indicates the existence probabilities that each pixel is assigned the respective regions of interest.

Here, the "existence probabilities" are the probabilities that each pixel exists in the respective regions of interest. The segmentation processing unit 20 assigns a region having the highest existence probability among the all regions of the three-dimensional image as the region of interest assigned to the pixel to generate a segmentation image. In the present embodiment, the existence probabilities for each pixel output from the segmentation processing unit 20 are stored in the storage unit 13.

Note that the trained model may be formed of, for example, a support vector machine (SVM), AdaBoost, or a random forest other than the neural network subjected to deep learning. Further, the segmentation processing unit 20 is not limited to a unit that includes the trained model subjected to machine learning. For example, the segmentation processing unit 20 may be a unit that extracts regions of interest by template matching or the like.

The image acquisition unit 21 acquires a three-dimensional image including regions of interest from the image storage server 3. The regions of interest are regions of structures, such as organs, bones, and cartilages, that can be diagnosis targets and to which the user pays attention. Note that in a case where a three-dimensional image is already stored in the storage unit 13, the image acquisition unit 21 may acquire the three-dimensional image from the storage unit 13. The image acquisition unit 21 acquires a segmentation image generated by the segmentation processing unit 20.

Figures 3, 4:
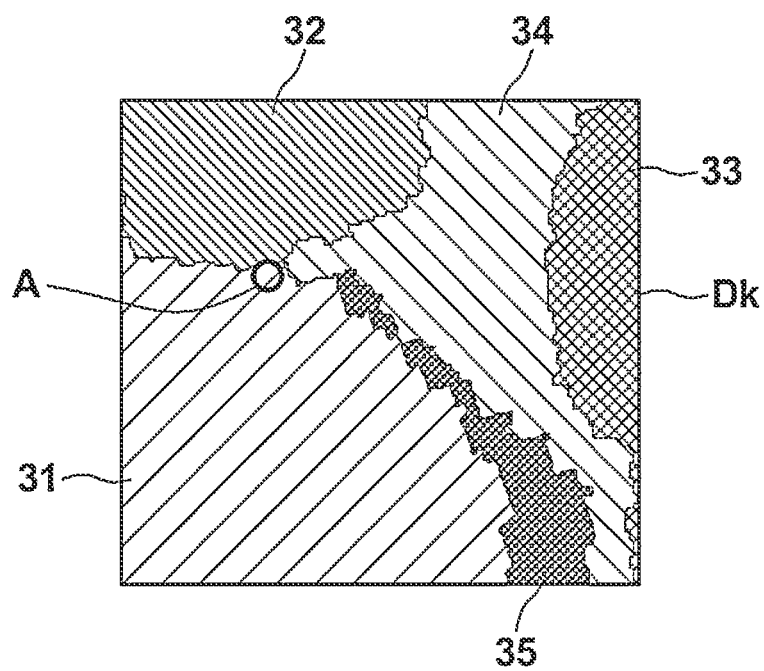
FIG. 3 is a diagram for explaining specification of a correction position on a segmentation image.
FIG. 4 is a diagram for explaining regions in a segmentation image.

The accepting unit 22 accepts position information indicating a position specified by the user on a segmentation image. FIG. 3 is a diagram for explaining specification of a correction position on a segmentation image Dk. The segmentation image Dk is one tomographic image among a plurality of tomographic images forming a three-dimensional image that is segmented into a plurality of regions by the segmentation processing unit 20 and is displayed on the display 14. Note that the displayed segmentation image Dk may be a tomographic image of any cross section, such as an axial cross section, a sagittal cross section, or a coronal cross section.

As illustrated in FIG. 3, in the segmentation image Dk, regions of interest 31 to 35 are assigned by the segmentation processing unit 20. The regions of interest 31 to 35 are included in the segmentation image Dk as masks. The masks are represented by different display patterns for the regions of interest 31 to 35 respectively, and the display patterns may be patterns that represent only outlines, hatched patterns, or patterns shaded in predetermined colors. In the following description, the regions of interest 31 to 35 mean masked regions in the segmentation image Dk.

On the segmentation image Dk illustrated in FIG. 3, the user uses the input unit 15 to specify a position at which the user wants to make a correction in an assigned region. The position can be specified by, for example, using a round cursor A displayed on the display 14. Note that the shape of the cursor A is not limited to a round shape and may be any shape, such as a rectangular shape, a triangular shape, or an arrow shape. The size of the cursor A can be set in advance to any size by the user. The size, shape, and the like of the cursor A may be set in advance for each diagnosis target part.

The accepting unit 22 accepts a correction instruction given by the user using the cursor A. In this case, the user uses the mouse of the input unit 15 to move the cursor A onto a region that is to be corrected. The accepting unit 22 accepts position information about the cursor A on the segmentation image Dk.

The preference-level acquisition unit 23 acquires on the basis of image information, the preference levels of regions to be assigned to the position on the segmentation image Dk indicated by the position information accepted by the accepting unit 22. To the segmentation image Dk, the names of parts represented by the regions of interest 31 to 35 are added as supplementary information when the segmentation process is performed by the segmentation processing unit 20. Further, the existence probability that each pixel is assigned each region of interest, the existence probability being output from the segmentation processing unit 20, is also added as supplementary information and saved in the storage unit 13.

FIG. 4 is a diagram for explaining the regions in the segmentation image. It is assumed as illustrated in FIG. 4 that, for example, the existence probability that the position on the segmentation image Dk indicated by the position information accepted by the accepting unit 22, that is, the region within the cursor A, is part a represented by the region of interest 31 is 45%, the existence probability that the position is part b represented by the region of interest 32 is 40%, the existence probability that the position is part c represented by the region of interest 34 is 10%, the existence probability that the position is a background represented by the region of interest 35 is 4%, and the existence probability that the position is part d represented by the region of interest 33 is 1%. Here, the "background" is a region that corresponds to none of the parts. For example, in a case where the segmentation processing unit 20 performs segmentation for only part a and part b, a region that does not correspond to part a or part b is the background. The region of interest 33 that represents part d is a region farthest from the cursor A, and therefore, the existence probability is lowest.

For the segmentation image Dk, the existence probabilities are output for each pixel. Therefore, each of the existence probabilities corresponding to the region within the cursor A is obtained as a representative value of the existence probabilities of all pixels that form the region within the cursor A. As the representative value, for example, the average, the median, the maximum value, or the minimum value of the existence probabilities can be used. The representative value of the existence probabilities of only pixels each having an existence probability higher than or equal to a predetermined threshold value may be assumed to be the existence probability corresponding to the region within the cursor A. The preference-level acquisition unit 23 acquires preference levels that are set such that the higher the existence probability illustrated in FIG. 4 is, the higher the preference level is.

The display control unit 24 performs control to display on the display 14, the three-dimensional image acquired by the image acquisition unit 21, the segmentation image Dk, and the like. The display control unit 24 performs control to display on the display 14, candidates for the region to be assigned on the basis of the preference levels acquired by the preference-level acquisition unit 23 so as to allow selection of the region to be assigned. Note that display on the display 14 by the display control unit 24, of candidates for the region to be assigned will be described in detail below. The image processing apparatus 1 of the present embodiment is configured as described above.

Figure 5:
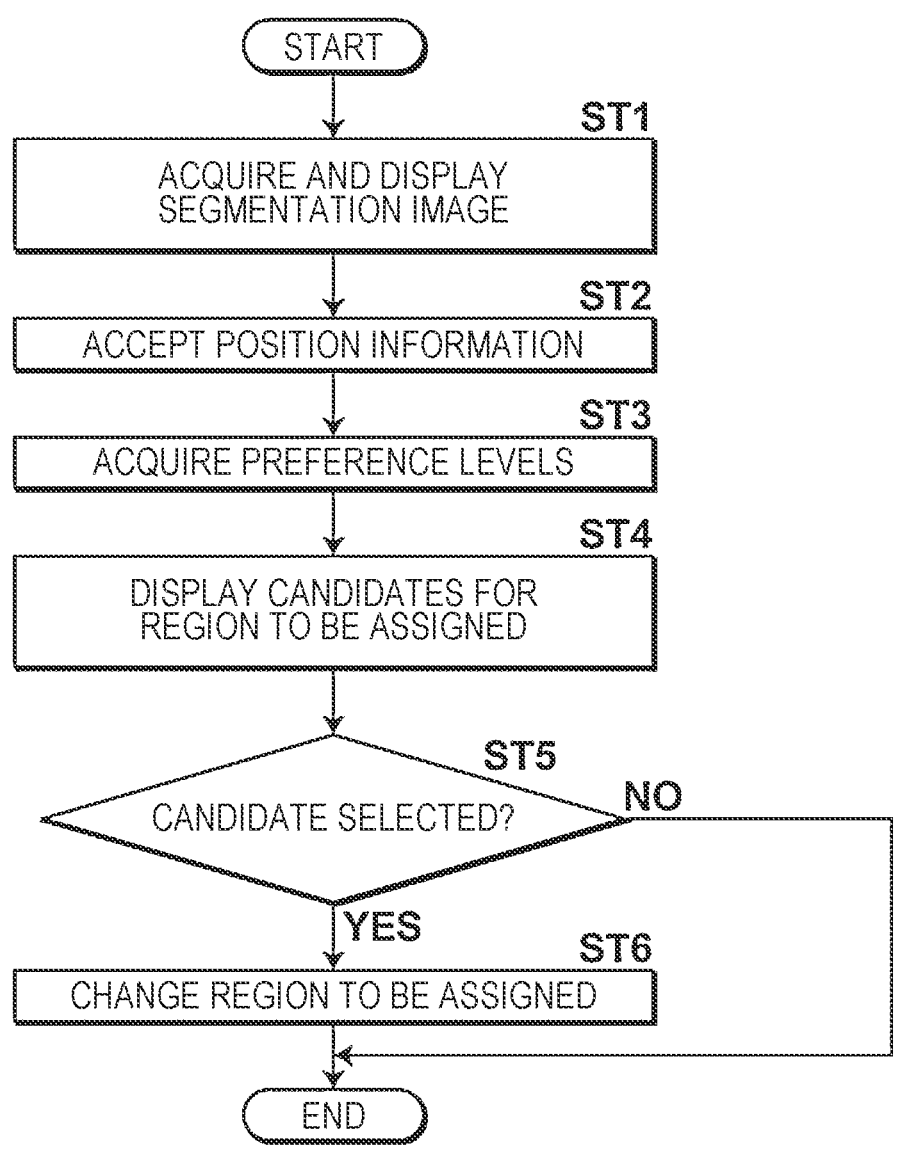
FIG. 5 is a flowchart illustrating processes performed in the present embodiment.

Now, a series of processes performed by the image processing apparatus 1 of the present embodiment is described. FIG. 5 is a flowchart illustrating processes performed in the present embodiment. As illustrated in FIG. 5, first, the image acquisition unit 21 acquires a segmentation image and the display control unit 24 displays the segmentation image on the display 14 (step ST1). Next, the accepting unit 22 accepts position information about the cursor A as described above (step ST2). The preference-level acquisition unit 23 acquires the preference levels of candidates for the region to be assigned (step ST3).

Next, the display control unit 24 displays the candidates for the region to be assigned on the display 14 (step ST4). As illustrated in FIG. 4, the existence probability that the region within the cursor A illustrated in FIG. 3 is part a is highest, and therefore, as a result of the segmentation process by the segmentation processing unit 20, the region within the cursor A is determined to be part a and represented by the display pattern of the region of interest 31.

However, the result of the segmentation process by the segmentation processing unit 20 is not always accurate and might not represent the actual regions of interest included in the segmentation image Dk. In such a case, currently, a correction is manually made to a region by using, for example, a shading tool. For example, in the case illustrated in FIG. 4, part b, part c, the background, and part d are candidates for the region to be assigned. As the number of such candidates increases, determination as to which region is to be assigned becomes complicated, and the user's operation becomes troublesome.

In the present embodiment, the display control unit 24 performs control to display on the display 14, candidates for the region to be assigned in descending order of preference level. FIG. 6 to FIG. 9 are diagrams for explaining an example of display of candidates for the region to be assigned. In the present embodiment, the preference levels of candidates for the region to be assigned acquired by the preference-level acquisition unit 23 are such that the preference level decreases in the order of part b, part c, the background, and part d as illustrated in FIG. 4.

Figure 6:
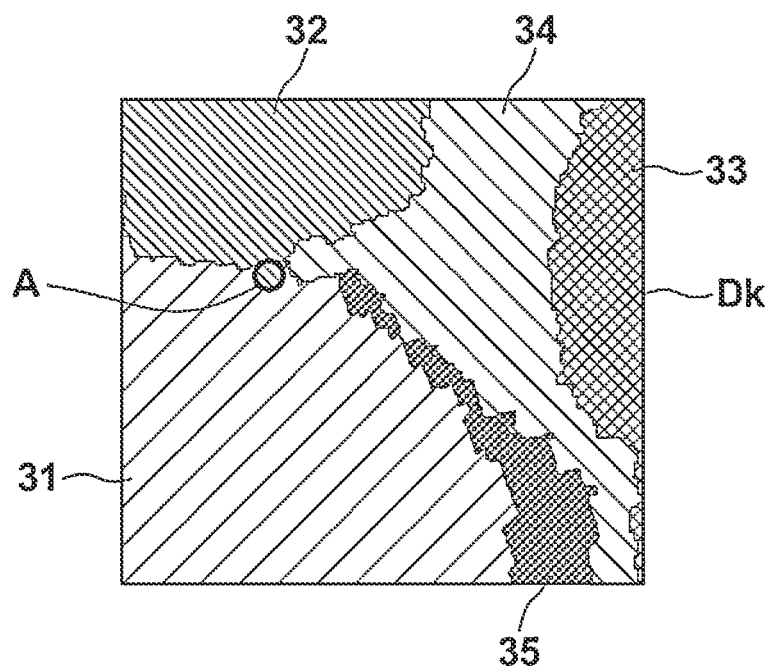
FIG. 6 is a diagram (1) for explaining an example of display of candidates for a region to be assigned.
Figure 7:
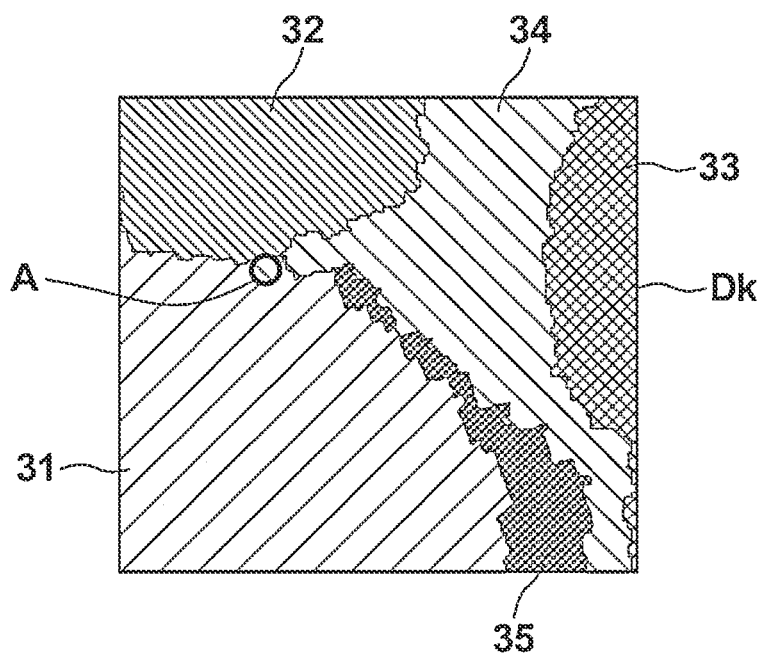
FIG. 7 is a diagram (2) for explaining an example of display of candidates for a region to be assigned.
Figure 8:
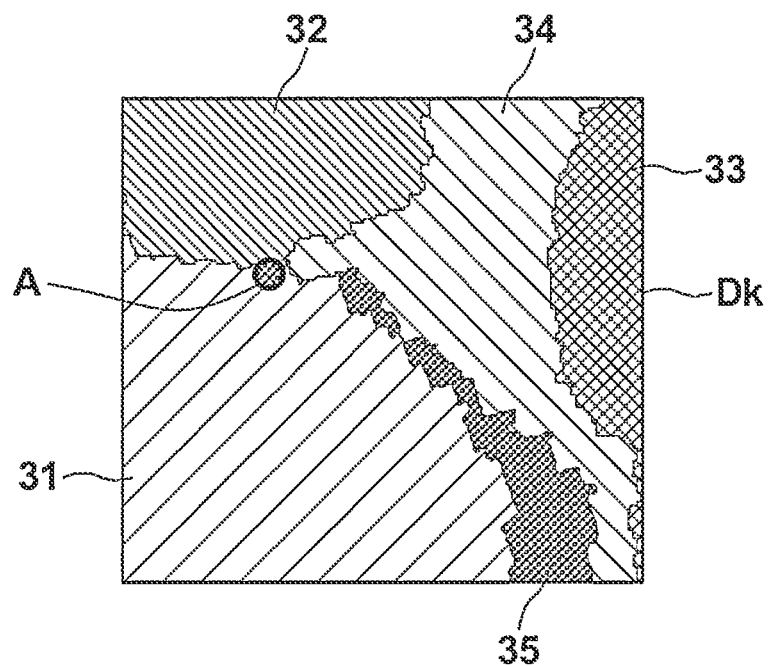
FIG. 8 is a diagram (3) for explaining an example of display of candidates for a region to be assigned.

First, as illustrated in FIG. 6, the display control unit 24 displays the region within the cursor A with the display pattern of the region of interest 32 representing "part b" having the highest preference level among the candidates for the region to be assigned. When the user operates the mouse wheel, the display control unit 24 displays the region within the cursor A with the display pattern of the region of interest 34 representing "part c" having the highest preference level next to part b among the candidates for the region to be assigned, as illustrated in FIG. 7. When the user operates the mouse wheel again, the display control unit 24 displays the region within the cursor A with the display pattern of the region of interest 35 representing the background having the highest preference level next to part c among the candidates for the region to be assigned, as illustrated in FIG. 8.

Figure 9:
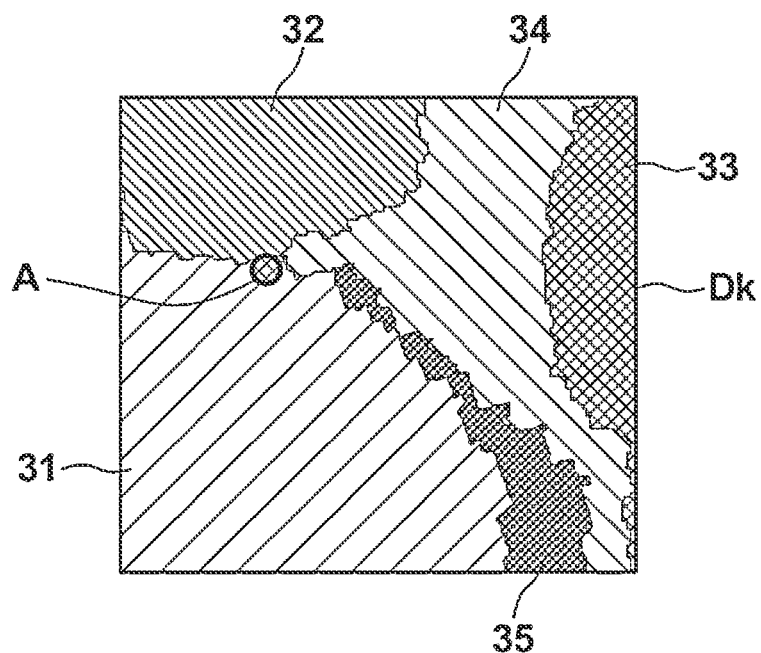
FIG. 9 is a diagram (4) for explaining an example of display of candidates for a region to be assigned.

When the user operates the mouse wheel again, the display control unit 24 displays the region within the cursor A with the display pattern of the region of interest 33 representing "part d" having the highest preference level next to the background among the candidates for the region to be assigned, as illustrated in FIG. 9. When the user subsequently operates the mouse wheel, the display control unit 24 restores the display to the original state illustrated in FIG. 4. The display control unit 24 repeatedly performs the above-described display control until the user selects a candidate for the region to be assigned.

Next, the CPU 11 determines whether a candidate for the region to be assigned is selected (step ST5). In a case where the CPU 11 determines that a candidate for the region to be assigned is selected by the user (YES in step ST5), the CPU 11 changes to the candidate region selected by the user, the region to be assigned (step ST6). An instruction for selecting a candidate can be given by, for example, clicking the right button of the mouse, which is the input unit 15, or by a combination of pressing a predetermined key and mouse clicking; however, the instruction may be given by any other operation.

On the other hand, in a case where the CPU 11 determines in step ST5 that a candidate for the region to be assigned is not selected by the user (NO in step ST5), the series of processes ends. An instruction for non-selection of a candidate can be given by, for example, pressing the escape (Esc) button, which is the input unit 15; however, the instruction may be given by any other operation.

As described above, with the present embodiment, for the position specified by the user, candidates for the region to be assigned are displayed on the display 14 on the basis of the preference levels of regions to be assigned so as to allow selection of the region to be assigned. Accordingly, even in a case where a large number of candidates for the region to be assigned are present, the user can easily check which region is to be assigned visually, and therefore, the user's operation can be made less troublesome while assignment of regions can be corrected as desired by the user.

Note that in the above-described embodiment, the preference-level acquisition unit 23 acquires the existence probabilities for each pixel; however, the technique of the present disclosure is not limited to this. For example, in a case where the segmentation processing unit 20 segments a target image into a plurality of regions and acquires, for each region, a score indicating the probability that the region is each of the regions instead of the existence probabilities for each pixel, the preference-level acquisition unit 23 may acquire preference levels on the basis of the scores of each region. The scores in this case may be probabilities.

Further, in the above-described embodiment, the display control unit 24 displays the region within the cursor A with each of the display patterns of the regions of interest 31 to 35 as illustrated in FIG. 4 and FIG. 6 to FIG. 9; however, the technique of the present disclosure is not limited to this. For example, the display control unit 24 may display the region within the cursor A in a color determined in advance for each region of interest. The display control unit 24 may display the region within the cursor A in association with at least one of score information, color information, or name information for each candidate for the region to be assigned.

Figure 10:
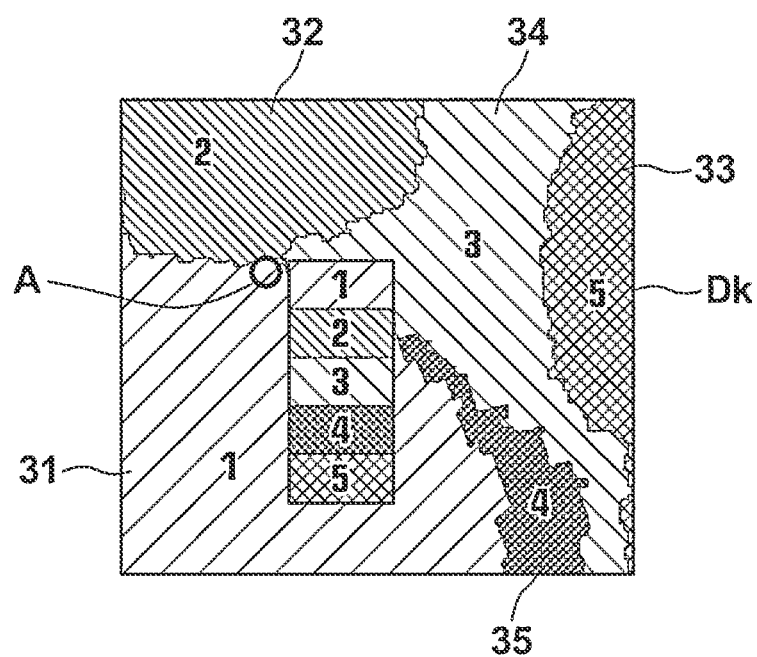
FIG. 10 is a diagram for explaining another example of display of candidates for a region to be assigned.

FIG. 10 is a diagram for explaining another example of display of candidates for the region to be assigned. As illustrated in FIG. 10, the display control unit 24 may display, for example, regions to be assigned that are numbered in descending order of preference level. In a case where a position is specified by the user, the display control unit 24 may display the display patterns each indicating the number and region in descending order of preference level near the specified position as a pull-down menu so as to allow selection. In this case, only the numbers may be displayed as a pull-down menu or only the display patterns may be displayed as a pull-down menu. Instead of the numbers, the names of the parts may be displayed. In this case, the name of a part having a higher preference level is displayed closer to the top of the pull-down menu.

In the above-described embodiment, the segmentation processing unit 20 is provided in the image processing apparatus 1; however, the technique of the present disclosure is not limited to this. For example, a segmentation image generated by an external segmentation processing unit may be saved in at least the storage unit 13 or the image storage server 3, and the image acquisition unit 21 may acquire the saved segmentation image. In this case, the segmentation image and existence probabilities, assigned to each pixel, output from the segmentation processing unit are saved in at least the storage unit 13 or the image storage server 3.

In the above-described embodiment, as the hardware configuration of the processing units that perform various processes, namely, for example, the segmentation processing unit 20, the image acquisition unit 21, the accepting unit 22, the preference-level acquisition unit 23, and the display control unit 24, various processors described below can be used. The various processors include, as described above, a CPU (central processing unit), which is a general-purpose processor executing software (program) to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform a specific process.

One processing unit may be configured as one of the various processors or a combination of two or more processors of the same type or different types (for example, a combination of a plurality of FPGAs or a combination of a CPU and an FPGA). Further, a plurality of processing units may be configured as one processor.

As the first example of configuring a plurality of processing units as one processor, a form is possible where one or more CPUs and software are combined to configure one processor, and the processor functions as the plurality of processing units, representative examples of which are computers including a client and a server. As the second example thereof, a form is possible where a processor is used in which the functions of the entire system including the plurality of processing units are implemented as one IC (integrated circuit) chip, a representative example of which is a system on chip (SoC). As described above, as the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

Note that in the image processing apparatus according to the present disclosure, the processor can acquire the preference levels on the basis of a score of each region of the plurality of regions acquired on the basis of a segmentation algorithm used in segmentation of the target image into the plurality of regions.

Further, in the image processing apparatus according to the present disclosure, the score of each region may be an existence probability for each pixel of the target image and may be an existence probability that each pixel exists in each region of the plurality of regions.

Further, in the image processing apparatus according to the present disclosure, the processor can perform control to display on the display, the candidates for the region to be assigned in descending order of preference level on the basis of input information input from an input device.

Further, in the image processing apparatus according to the present disclosure, the processor can perform control to display the position specified by the user in a color set in advance for each of the candidates for the region to be assigned.

Further, in the image processing apparatus according to the present disclosure, the processor can perform control to display the position specified by the user in association with at least one of score information, color information, or name information for each of the candidates for the region to be assigned.

With the present disclosure, correction of region assignment can be made as desired by a user while the user's operation is made less troublesome.

What is claimed is:

1. An image processing apparatus comprising:
a processor that is configured to:
acquire a segmentation image obtained by segmenting a target image into a plurality of regions;
accept position information indicating a position specified by a user on the segmentation image;
acquire on the basis of image information, preference levels of the plurality of regions from which a region to be assigned to the position on the segmentation image indicated by the position information is selected; and
perform control to display on a display, the plurality of regions as candidates for the region to be assigned so as to allow selection of the region to be assigned from the candidates, on the basis of the acquired preference levels.

2. The image processing apparatus according to claim 1, wherein the processor acquires the preference levels on the basis of a score of each region of the plurality of regions acquired on the basis of a segmentation algorithm used in segmentation of the target image into the plurality of regions.

3. The image processing apparatus according to claim 2, wherein the score of each region is an existence probability for each pixel of the target image and is an existence probability that each pixel exists in each region of the plurality of regions.

4. The image processing apparatus according to claim 1, wherein the processor performs control to display on the display, the candidates for the region to be assigned in descending order of preference level on the basis of input information input from an input device.

5. The image processing apparatus according to claim 2, wherein the processor performs control to display on the display, the candidates for the region to be assigned in descending order of preference level on the basis of input information input from an input device.

6. The image processing apparatus according to claim 3, wherein the processor performs control to display on the display, the candidates for the region to be assigned in descending order of preference level on the basis of input information input from an input device.

7. The image processing apparatus according to claim 1, wherein the processor performs control to display the position specified by the user in a color set for each of the candidates for the region to be assigned.

8. The image processing apparatus according to claim 2, wherein the processor performs control to display the position specified by the user in a color set for each of the candidates for the region to be assigned.

9. The image processing apparatus according to claim 3, wherein the processor performs control to display the position specified by the user in a color set for each of the candidates for the region to be assigned.

10. The image processing apparatus according to claim 1, wherein the processor performs control to display the position specified by the user in association with at least one of score information, color information, or name information for each of the candidates for the region to be assigned.

11. The image processing apparatus according to claim 2, wherein the processor performs control to display the position specified by the user in association with at least one of score information, color information, or name information for each of the candidates for the region to be assigned.

12. The image processing apparatus according to claim 3, wherein the processor performs control to display the position specified by the user in association with at least one of score information, color information, or name information for each of the candidates for the region to be assigned.

13. An image processing method comprising:
by a processor,
  acquiring a segmentation image obtained by segmenting a target image into a plurality of regions;
  accepting position information indicating a position specified by a user on the segmentation image;
  acquiring on the basis of image information, preference levels of the plurality of regions from which a region to be assigned to the position on the segmentation image indicated by the accepted position information is selected; and
  performing control to display on a display, the plurality of regions as candidates for the region to be assigned so as to allow selection of the region to be assigned from the candidates, on the basis of the acquired preference levels.

14. A non-transitory computer-readable storage medium storing an image processing program for causing a computer to:
  acquire a segmentation image obtained by segmenting a target image into a plurality of regions;
  accept position information indicating a position specified by a user on the segmentation image;
  acquire on the basis of image information, preference levels of the plurality of regions from which a region to be assigned to the position on the segmentation image indicated by the accepted position information is selected; and
  perform control to display on a display, the plurality of regions as candidates for the region to be assigned so as to allow selection of the region to be assigned from the candidates, on the basis of the acquired preference levels.

15. The image processing apparatus according to claim 1, wherein the preference level of each region of the plurality of regions is an existence probability that each pixel of the target image exists in each region of the plurality of regions.

16. The image processing apparatus according to claim 1, wherein the processor performs control to display on the display, the candidates for the region to be assigned in a sorting order of preference level.

\* \* \* \* \*